US008349161B2

(12) United States Patent  (10) Patent No.: US 8,349,161 B2
Gomi et al.  (45) Date of Patent: Jan. 8, 2013

(54) ELECTROPHORESIS DEVICE AND PUMP

(75) Inventors: Takashi Gomi, Hitachinaka (JP); Ryoji Inaba, Hitachinaka (JP); Taro Nakazawa, Hitachinaka (JP); Takeshi Ohura, Hitachinaka (JP); Mari Kotoura, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/263,304

(22) PCT Filed: Apr. 6, 2010

(86) PCT No.: PCT/JP2010/056241
§ 371 (c)(1),
(2), (4) Date: Oct. 6, 2011

(87) PCT Pub. No.: WO2010/116999
PCT Pub. Date: Oct. 14, 2010

(65) Prior Publication Data
US 2012/0031762 A1  Feb. 9, 2012

(30) Foreign Application Priority Data
Apr. 10, 2009 (JP) ................... 2009-096307

(51) Int. Cl.
*G01N 27/453* (2006.01)
(52) U.S. Cl. ............................. 204/604; 204/605; 92/61
(58) Field of Classification Search .................. 204/453, 204/455, 604, 605; 417/555.1; 92/169.1, 92/61
See application file for complete search history.

(56) References Cited

U.S. PATENT DOCUMENTS
4,056,335 A * 11/1977 Secrist ........................ 417/431
2008/0116073 A1 5/2008 Shoji et al.

FOREIGN PATENT DOCUMENTS
JP 3136062 U 9/2007
JP 2008-128851 6/2008

* cited by examiner

*Primary Examiner* — Kaj K Olsen
(74) *Attorney, Agent, or Firm* — McDermott Will & Emery LLP

(57) ABSTRACT

Bubbles can be removed regardless of an individual difference of a pump to fill an electrophoresis medium into a capillary. Of flow passages formed between an inner side surface of a container for accommodating the electrophoresis medium and a side surface of a plunger, one of the flow passages causing an electrophoresis medium to be easily stagnant is formed to have the cross-sectional area larger than the cross-sectional area of the other flow passage on the opposite side. In other words, the flow passage portion causing the electrophoresis medium to be easily stagnant is formed in such a manner as to increase a flow amount of the electrophoresis medium. This can eliminate a region having an extremely small amount of electrophoresis medium flow in the pump.

20 Claims, 10 Drawing Sheets (a)

(b)

(a)

(b)

(a)

(b)

(a)

(b)

(a)

(b)

(a)

(b)

(a)

(b)

(a)

(b)

(a)

(b)

(a)

(b)

ELECTROPHORESIS DEVICE AND PUMP

RELATED APPLICATIONS

This application is the U.S. National Phase under 35 U.S.C. §371 of International Application No. PCT/JP2010/056241, filed on Apr. 6, 2010, which in turn claims the benefit of Japanese Application No. 2009-096307, filed on Apr. 10, 2009, the disclosures of which Applications are incorporated by reference herein.

TECHNICAL FIELD

The present invention relates to an electrophoresis device and relates to a structure of a pump to fill an electrophoresis medium into a capillary, for example. However, the structure of the pump in the present invention is not limited to the electrophoresis device and is also applicable to be used as a plunger pump for liquid chromatography, for example.

BACKGROUND ART

A capillary electrophoresis device is widely used as a device for analyzing nucleic acids, proteins or the like. The capillary electrophoresis device is a device that analyzes a sample in the following manner. Specifically, an electrophoresis medium (a separation medium) such as a polymer gel or a polymer solution is filled into a narrow tube called a capillary, and a high voltage is applied thereto. The sample is analyzed by utilizing an electrophoresis mobility difference caused by a molecular size difference.

The capillary electrophoresis device mainly includes: a capillary; a power source configured to apply a high voltage between ends of the capillary; an irradiation system configured to emit laser light onto an inspection region; a photoreceptor optical system configured to detect fluorescence generated due to the irradiation of the laser light; a temperature conditioning unit configured to control the temperature of the capillary; a filling unit configured to fill the electrophoresis medium into the capillary; and the like.

Meanwhile, the filling unit needs to inject an electrophoresis medium having a viscosity several hundred times higher than that of water into a capillary having an inner diameter of approximately 50 μm. Thus, the filling unit is required to be capable of generating a pressure of even several mega Pascals. For this reason, a plunger pump is used for the filling unit, for example.

In addition, the capillary electrophoresis device applies a high voltage of several to tens of kilovolts to the capillary during electrophoresis. Thus, if bubbles are present in a flow passage of the electrophoresis medium, the flow passage is electrically blocked in some cases. In such cases, a high voltage is generated in the electrophoresis medium blocked by the bubbles and thus might cause a discharge phenomenon. The discharge sometimes destroys the device. For this reason, the bubbles need to be removed from the flow passage of the electrophoresis medium before the electrophoresis is started.

PRIOR ART DOCUMENT

Patent Document
Patent Document 1: Japanese Patent Application Publication No. 2008-128851

SUMMARY OF THE INVENTION

Problem to be Solved by the Invention

The inventors of the present application have earnestly studied a pump structure of the electrophoresis device and have found that a plunger pump has an individual difference in the degree of bubble exiting. As one of the causes of the individual difference, a dimensional variation of a component, assembly variation thereof or the like is conceivable. For example, it is believed that if the radial thickness of the plunger, a clearance between the plunger and a plunger hole or the like varies with the pump, a change occurs in a flow of the electrophoresis medium and thus causes a variation in the degree of the bubble exiting.

The present invention aims to propose an electrophoresis device having a bubble removal performance less influenced by an individual difference of a pump to fill an electrophoresis medium into a capillary.
Means for Solving the Problem The present invention relates to formation of flow passages between an inner side surface of a container accommodating an electrophoresis medium and a side surface of a plunger in such a manner that the cross-sectional area of one of the flow passages on a side where the electrophoresis medium is easily stagnant due to the structure is larger than the cross-sectional area of the flow passage on an opposite side. This formation increases a flow amount of the electrophoresis medium in the flow passage portion where stagnation due to the structure easily occurs.
Effects of the Invention The present invention can eliminate a flow passage causing the electrophoresis medium to be easily stagnant regardless of an individual difference of a pump forming an electrophoresis device. Thereby, a viscous force of the electrophoresis medium can act on bubbles regardless of the location of the bubbles, and the bubbles can be removed from inside the pump.

MODES FOR CARRYING OUT THE INVENTION

Hereinafter, embodiments of the present invention are given in order based on the drawings. Note that the drawings are created mainly for the purpose of explaining the invention and are not limited to the scope of the invention.

(1) Consideration of Bubble Residual

Figure 1:
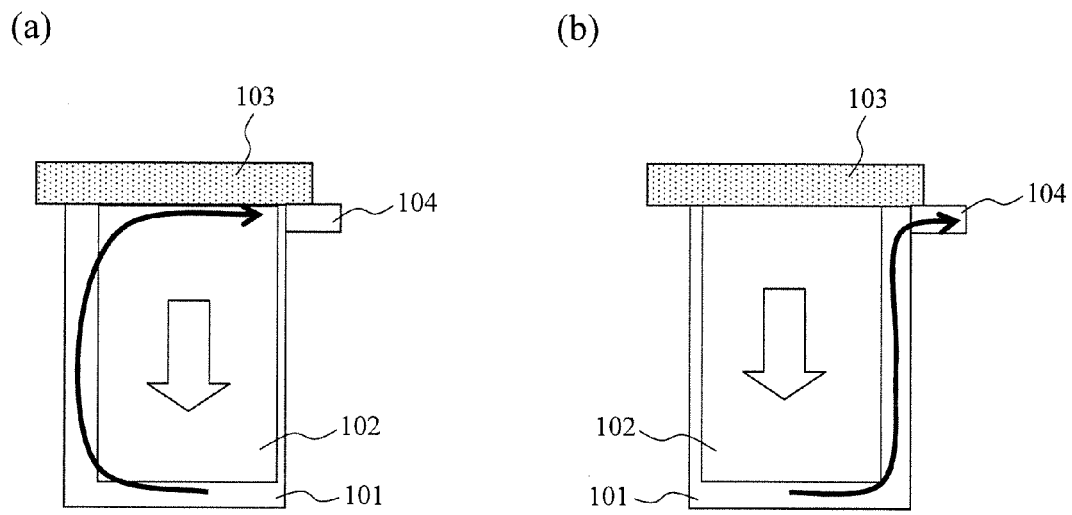
FIGS. 1a and 1b is a diagram for explaining a difference between electrophoresis medium flows resulting from a difference in fitting relationship between a plunger and a plunger hole.

Firstly, a description is given of a consideration by the inventors of a cause of an individual difference of a plunger pump in bubble residual. FIG. 1 shows examples of two positional relationships conceivable for a plunger hole and a plunger. Specifically, a plunger hole 101 is a tubular container (so-called a cylinder) having a bottom surface and includes an inlet (unillustrated) through which an electrophoresis medium flows in and an outlet 104 through which the electrophoresis medium flows out. A plunger 102 is fitted in the plunger hole 101 in such a manner as to be freely movable in a direction along an inner wall of the plunger hole 101 and is a member (so-called a piston) which discharges the electrophoresis medium from the outlet 104 by utilizing a pressure generated in moving in an arrow direction. Incidentally, an opening portion of the plunger hole 101 is sealed by a plunger seal 103.

Part (a) of FIG. 1 shows an example of a case where the plunger 102 is fitted in the plunger hole 101 in such a manner as to be eccentric toward the right of the drawing (toward the outlet 104). In this case, a clearance formed between an inner side surface of the plunger hole 101 and a side surface of the plunger 102 has an asymmetrical shape. That is, a portion of the clearance on the left side of the drawing is larger than a portion of the clearance on the right side of the drawing. At this time, the plunger 102 has a smaller flow passage resistance on a left side surface and a larger flow passage resistance on a right side surface. This means that a lot of electrophoresis medium flows through the clearance portion having the smaller flow passage resistance on the left side when the plunger 102 is thrust down, as shown by the arrow.

Part (b) of FIG. 1 shows an example of a case where the plunger 102 is fitted in the plunger hole 101 in such a manner as to be eccentric toward the left of the drawing (opposite from the outlet 104). Also in this case, a clearance formed between an inner side surface of the plunger hole 101 and a side surface of the plunger 102 has an asymmetrical shape. However, a portion of the clearance on the right side of the drawing is larger than a portion of the clearance on the left side of the drawing. At this time, the plunger 102 has a smaller flow passage resistance on a right side surface and a larger flow passage resistance on a left side surface. This means that a lot of electrophoresis medium flows through the clearance portion having the smaller flow passage resistance on the right side when the plunger 102 is thrust down, as shown by the arrow.

In a conventional design, an axis of the plunger hole 101 and an axis of the plunger 102 coincide with each other, when the plunger 102 is fitted in the plunger hole 101. However, once the axis center is just displaced due to a dimensional variation or an assembly variation, the flow of the electrophoresis medium changes largely as shown in FIG. 1. The flow difference is considered to be one of the causes of an individual difference in the degree of bubble residual. Hence, a description is given below of a structure of a plunger pump conceived by the inventors which has the bubble removal performance less influenced by the individual difference.

(2) Embodiment 1

(2-1) Overall Configuration of Capillary Electrophoresis Device

Figure 2:
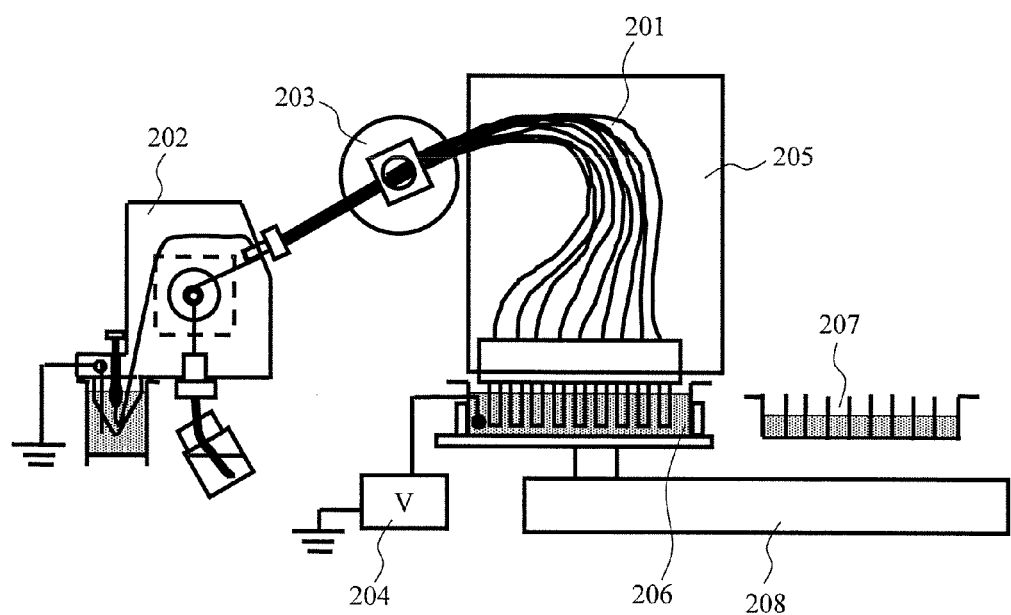
FIG. 2 is a diagram showing an overall configuration example of an electrophoresis device according to an embodiment.

Firstly, a description is given of a configuration example of a capillary electrophoresis device common to embodiments. FIG. 2 shows a schematic configuration of the capillary electrophoresis device. The capillary electrophoresis device includes: at least one capillary (a capillary array 201) serving as an energization channel in electrophoresis; a plunger pump 202 to fill a polymer solution or another electrophoresis medium into the capillary; an optical detection mechanism 203 to optically detect a sample separated due to the electrophoresis; a voltage source 204 to apply a high voltage to the capillary; a constant temperature oven 205 to maintain a peripheral environment of the capillary at a constant temperature; and a conveyor 208 to convey vessels 206 and 207 to the cathode end side of the capillary.

In the case of FIG. 2, the vessel 206 contains a buffer solution or purified water, while the vessel 207 contains a sample.

FIG. 2 shows the capillary array 201 formed by multiple capillaries, but a single capillary may be used. In this embodiment, glass narrow tubes each having an inner diameter of several ten to several hundred micron meters and an outer diameter of several hundred micron meters are used as the capillaries. The capillaries each having a length of several centimeters to several tens of centimeters are used depending on the content of the analysis. In addition, a surface of each capillary is coated with a polyimide thin film having a film thickness of several micron meters, and thus the strength is enhanced. The polyimide thin film, however, is removed only in a range of an approximately several millimeter length so that excitation light can enter the capillary, the range corresponding to a regional portion where a detection portion is arranged. The optical detection mechanism 203 is formed at a position several centimeters to several tens of centimeters away from a sample injection end of the capillary so that the sample separated by the electrophoresis can be detected.

The optical detection mechanism 203 includes a light irradiation unit (for example, a laser light source) to emit light onto the detection portion of the capillary and a light detection mechanism (for example, a CCD camera) to detect light emitted from the sample. Note that the optical detection mechanism 203 includes other various mechanisms. For example, some detection systems employ a scanning method. The scanning method also includes ones employing: a combination of a mechanism for scanning laser with a galvanometer mirror with a mechanism for detecting fluorescence having a particular wavelength with a rotary filter; and a mechanism of reciprocating an objective lens in a confocal optical system. The scanning method also includes a one employing a mechanism for emitting excitation light onto a particular portion of a capillary by using a cone lens. The scanning method also includes a one employing a mechanism in which tip ends of capillaries are arranged in a matrix form and tip end surfaces thereof serve as detection surfaces.

(2-2) Configuration of Plunger Pump and Expected Effects

Figure 3:
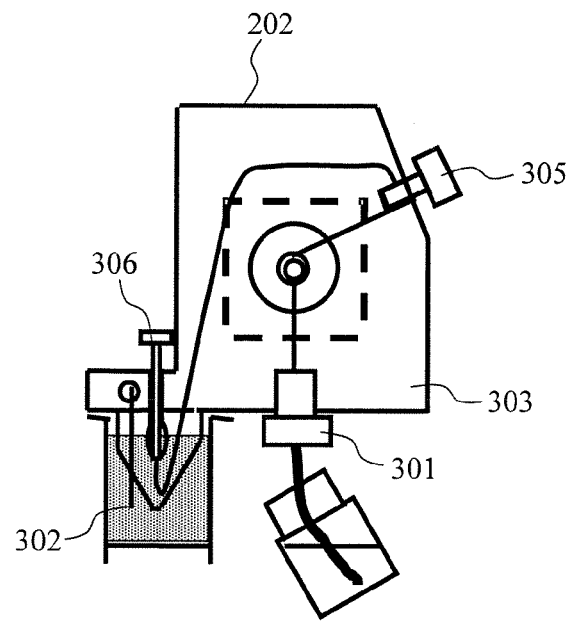
FIGS. 3a and 3b is a diagram for explaining modes of fitting a plunger pump.
Figure 3:
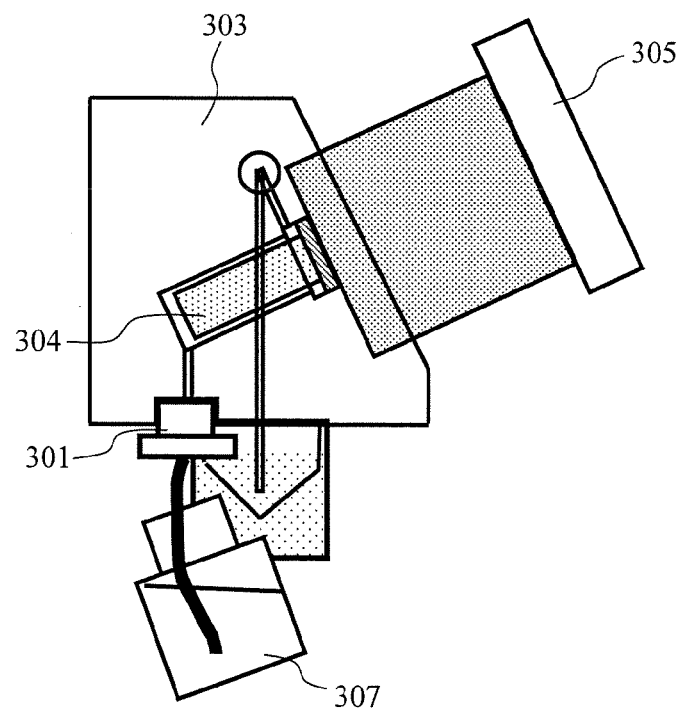

FIG. 3 shows a structure example of the plunger pump 202. The plunger pump 202 is connected to one end of the capillary array 201. Part (b) of FIG. 3 is a diagram showing a structure in Part (a) of FIG. 3 in an enlarged manner. As shown in FIG. 3, a flow passage from a check valve 301 to an anode 302 is provided in a pump head 303, and a plunger 304 and a capillary connection portion 305 are provided in the course of the flow passage. Note that an acrylic block having characteristics of both insulation and transmittance is used for the pump head 303 so that a current can flow in the flow passage in the electrophoresis and bubbles in the flow passage can be observed. In addition, a pin valve 306 is provided on the anode side. The pin valve 306 automatically operates with a solenoid. When the pin valve 306 is closed and the plunger 304 is thrust, the capillary array 201 can be filled with the electrophoresis medium. Note that a backward flow of the electrophoresis medium to an electrophoresis medium vessel 307 is prevented by closing the check valve 301.

Figure 4:
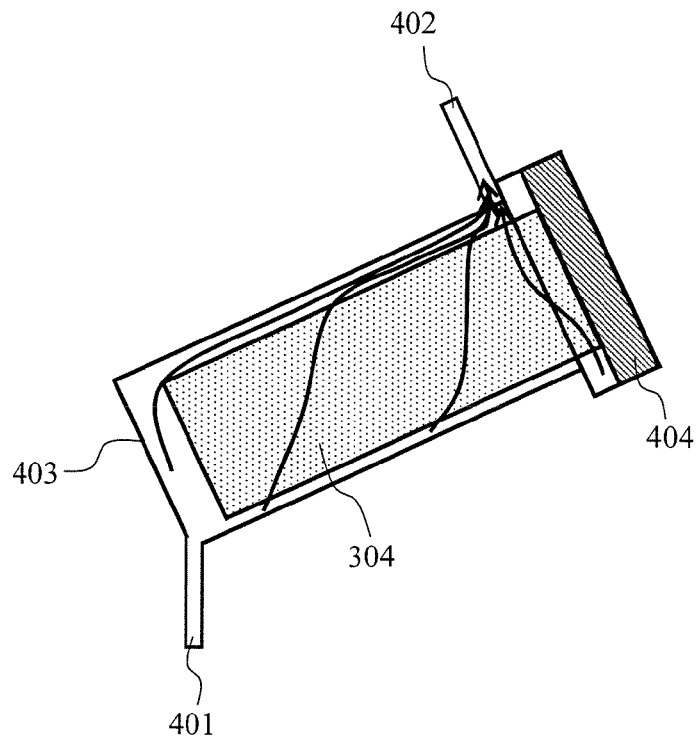
FIGS. 4a and 4b is a diagram for explaining fitting structures of the plunger and the plunger hole according to Embodiment 1.
Figure 4:
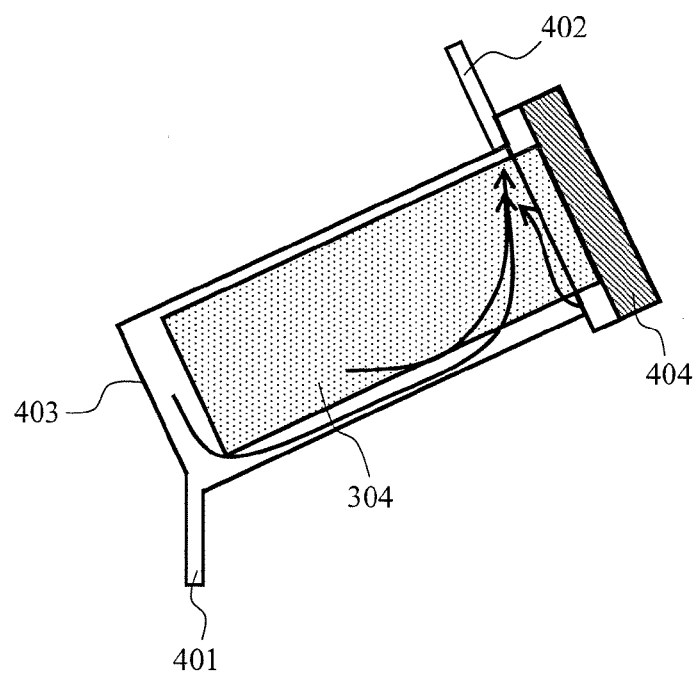

FIG. 4 shows fitting structures of the plunger 304 and a plunger hole 403. In this embodiment, both the plunger 304 and the plunger hole 403 have a circular cross-sectional shape. Moreover, the plunger 304 and the plunger hole 403 are fitted obliquely with respect to a vertical direction. Furthermore, as shown in FIG. 4, an inlet 401 to introduce the electrophoresis medium is formed in the lowermost portion of the plunger hole 403, and an outlet 402 to introduce the electrophoresis medium in the uppermost portion of the plunger hole 403. In Embodiment 1, however, as long as the inlet 401 is formed at a lower position than the outlet 402 is, the inlet 401 may be formed at any position of the plunger hole 403. Note that an opening of the plunger hole 403 is closed by a plunger seal 404 at an upper position than the outlet 402.

Based on the consideration above, this embodiment employs a structure in which an axis of the plunger hole 403 and an axis of the plunger 304 are intentionally shifted from each other. Specifically, a fitting structure shown in Part (a) of FIG. 4 is employed. In other words, the structure is employed in which a fitting position is designed in the following manner. Specifically, a clearance portion, of a clearance formed between a side surface of the plunger hole 403 and a side surface of the plunger 304, formed on an upper side in the vertical direction is made larger than the other.

For example, when the plunger 304 has a diameter of approximately 3 mm to 5 mm, an inclination in a fitting direction of approximately 25° with respect to a horizontal surface (65° with respect to the vertical direction), and an allowance of 0.05 mm, it is preferable to design the clearance as follows.

A clearance portion formed on the upper surface side of the plunger hole 403 and the plunger 304: approximately 0.2 mm
  A clearance portion formed on the lower surface side of the plunger hole 403 and the plunger 304: approximately 0.1 mm
  A clearance portion formed between a bottom surface of the plunger 304 and a bottom surface of the plunger hole 403 at the maximum thrusting of the plunger 304: approximately 0.2 mm to 0.4 mm When these conditions are satisfied, the clearance portion formed on the upper surface side of the plunger hole 403 and the plunger 304 can be prevented from being smaller than the clearance portion formed on the lower surface side of the plunger hole 403 and the plunger 304, even if a dimensional variation or an assembly variation is present. Incidentally, under these conditions, when the plunger 304 is fitted in the plunger hole 403 in such a manner as to be shifted to below and when a shifting amount is the maximum, the clearance portion on the upper surface side is 0.25 mm and the clearance portion on the lower surface side is 0.05 mm. On the other hand, when the plunger 304 is fitted in such a manner as to be shifted to above and when the shifting amount is the maximum, the clearance portion on the upper surface side is 0.15 mm and the clearance portion on the lower surface side is 0.15 mm.

Thus, use of the plunger pump 202 according to the embodiment makes it possible for the plunger 304 to always have a flow passage resistance on the upper surface side which is smaller than a flow passage resistance on the lower surface side. This means that a structure of a plunger pump having no individual difference of the degree of bubble exiting can be achieved.

Subsequently, how bubbles near the plunger exit will be described by using Part (a) of FIG. 4.

(a) How bubbles on the side surface of the plunger 304 flow
  When the plunger 304 is thrust, the electrophoresis medium on the side surface of the plunger 304 flows to the outlet 402 located in the uppermost portion of the plunger hole 403. At this time, both an upward viscous force and an upward buoyancy due to the electrophoresis medium flow act on bubbles. Thus, the bubbles move with flow of the electrophoresis medium and go out through the outlet 402.

(b) How bubbles on the bottom surface of the plunger 304 flow
  When the plunger 304 is thrust, the electrophoresis medium on the bottom surface of the plunger 304 moves in such a manner as to pass on the upper surface side having the smallest flow passage resistance in the side surfaces of the plunger 304 and reaches the outlet 402 located in the uppermost portion of the plunger hole 403. Also in this case, both an upward viscous force and an upward buoyancy due to the electrophoresis medium flow act on bubbles. Thus, the bubbles move with flow of the electrophoresis medium and go out through the outlet 402.

As described above, in the case of the plunger pump 202 according to the embodiment, it is possible to match the directions of the buoyancy and the viscous force acting on the bubbles. This causes the bubbles near the plunger not to stay on the plunger 304 but to easily go out from the outlet 402. Consequently, the bubbles can be removed with a small amount of polymer, and thus a consumption amount of the expensive polymer can be reduced.

(2-3) Comparison Example

How the bubbles flow when the plunger pump 202 according to the embodiment is not used will be described for a reference purpose. If the aforementioned fitting structure is not employed, there is a possibility that the clearance portion formed on the lower surface side of the plunger hole 403 and the plunger 304 is wider than the clearance portion formed on the upper surface side of the plunger hole 403 and the plunger 304, as shown in Part (b) of FIG. 4.

Also in this case, it goes without saying that the electrophoresis medium tends to flow to the outlet 402 through a path having the smallest flow passage resistance when the plunger 304 is thrust. In other words, the electrophoresis medium tends to flow to the outlet 402 passing on the lower surface side of the plunger 304. This means that a downward flow occurs in the electrophoresis medium near the bottom surface of the plunger 304. Consequently, both a downward viscous force due to the electrophoresis medium and the upward buoyancy act on bubbles near the bottom surface of the plunger 304. That is, forces in directions opposite to each other act on the bubbles. Thus, there is a possibility that the bubbles do not exit depending on the size or the shape of the bubbles.

(3) Embodiment 2
  Subsequently, a description is given of a second embodiment of the capillary electrophoresis device. A basic structure of the capillary electrophoresis device according to this embodiment is the same as that of Embodiment 1. Hereinafter, a description is given of a structure of the plunger pump 202 according to the embodiment.

Figure 5:
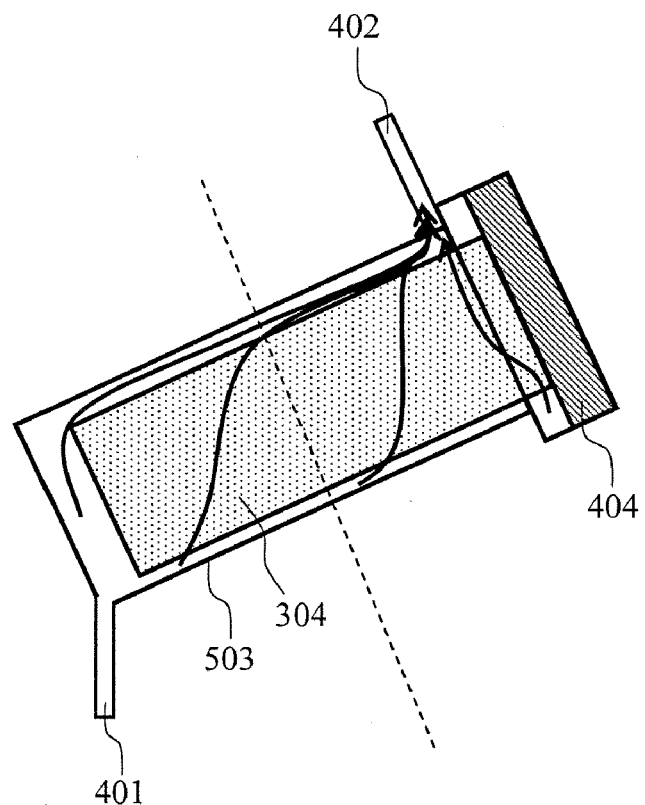
FIGS. 5a and 5b is a diagram for explaining fitting structures of the plunger and the plunger hole according to Embodiment 2.
Figure 5:
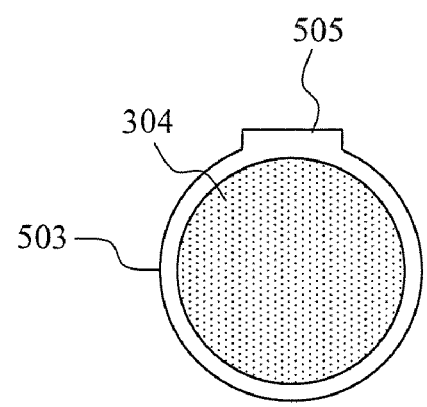

FIG. 5 shows fitting structures of the plunger 304 and a plunger hole 503 forming the plunger pump 202 according to this embodiment. Also in this embodiment, the plunger 304 and the plunger hole 503 are installed obliquely to the vertical direction, as shown in Part (a) of FIG. 5. In addition, the inlet 401 to introduce the electrophoresis medium is formed in the lowermost portion of the plunger hole 503, and the outlet 402 to lead out the electrophoresis medium is formed in the uppermost portion of the plunger hole 503.

The difference from Embodiment 1 lies in a cross-sectional structure of the plunger hole 503. Part (b) of FIG. 5 shows a cross-sectional shape corresponding to a part taken along the dotted line in Part (a) of FIG. 5. In this embodiment, as shown in Part (b) of FIG. 5, a groove 505 extending in an extending direction of the plunger hole 503 is formed on the upper surface side, of the plunger hole 503, in the vertical direction. Thus, an inner diameter of the portion in which the groove 505 is formed is formed to be larger than an inner diameter of the other portion.

For example, when the plunger 304 has a diameter of approximately 3 mm to 5 mm, an inclination in a fitting direction of approximately 25° with respect to a horizontal surface (65° with respect to the vertical direction), and an allowance of 0.05 mm, it is preferable to design the clearance as follows.

A clearance portion formed between the bottom surface of the groove 505 (on the upper surface side of the plunger hole 503) and the plunger 304: approximately 0.2 mm A clearance portion formed on the lower surface side of the plunger hole 503 and the plunger 304: approximately 0.1 mm A clearance portion formed between a bottom surface of the plunger 304 and a bottom surface of the plunger hole 503 at the maximum thrusting of the plunger 304: approximately 0.2 mm to 0.4 mm.

When these conditions are satisfied, the clearance portion formed on the upper surface side of the groove 505 and the plunger 304 can be prevented from being smaller than the clearance portion formed on the lower surface side of the plunger hole 503 and the plunger 304, even if a dimensional variation or an assembly variation is present. The dimensions are determined in consideration of allowances, as a matter of course.

Alternatively, in the case of using the groove 505 as in this embodiment, the fitting position of the plunger 304 and the plunger hole 503 can be designed so that an axis of the plunger hole 503 and the axis of the plunger 304 can coincide with each other, instead of the case where the axis of the plunger hole 503 and the axis of the plunger 304 are shifted from each other as in Embodiment 1. Part (b) of FIG. 5 corresponds to the case where the plunger hole 503 and the plunger 304 are fitted coaxially.

Thus, use of the plunger pump 202 according to this embodiment makes it possible for the plunger 304 to always have a flow passage resistance on the upper surface side which is smaller than a flow passage resistance on the lower surface side. This means that a structure of a plunger pump having no individual difference of the degree of bubble exiting can be achieved.

In this embodiment, bubbles near the plunger go out in the following manner.

(a) How bubbles on the side surface of the plunger 304 flow

When the plunger 304 is thrust, the electrophoresis medium on the side surface of the plunger 304 flows to the outlet 402 located in the uppermost portion of the plunger hole 503 in such a way as to be guided by the groove 505. At this time, both an upward viscous force and an upward buoyancy due to the electrophoresis medium flow act on bubbles. Thus, the bubbles move with flow of the electrophoresis medium and go out through the outlet 402.

(b) How bubbles on the bottom surface of the plunger 304 flow

When the plunger 304 is thrust, the electrophoresis medium on the bottom surface of the plunger 304 moves in such a manner as to pass on the upper surface side (the portion where the groove 505 is formed) having the smallest flow passage resistance in the side surfaces of the plunger 304 and reaches the outlet 402 located in the uppermost portion of the plunger hole 503. Also in this case, both an upward viscous force and an upward buoyancy due to the electrophoresis medium flow act on bubbles. Thus, the bubbles move with flow of the electrophoresis medium and go out through the outlet 402.

As described above, also in the case of the plunger pump 202 according to the embodiment, it is possible to match the directions of the buoyancy and the viscous force acting on the bubbles. This causes the bubbles near the plunger not to stay on the plunger 304 but to easily go out from the outlet 402. Consequently, the bubbles can be removed with a small amount of polymer, and thus a consumption amount of the expensive polymer can be reduced.

(4) Embodiment 3

Subsequently, a description is given of a third embodiment of the capillary electrophoresis device. A basic structure of the capillary electrophoresis device according to this embodiment is the same as that of Embodiment 1. Hereinafter, a description is given of a structure of the plunger pump 202 according to the embodiment.

Figure 6:
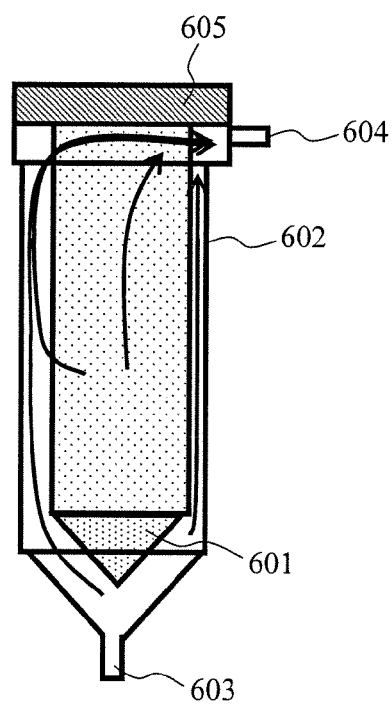
FIGS. 6a and 6b is a diagram for explaining fitting structures of the plunger and the plunger hole according to Embodiment 3.
Figure 6:
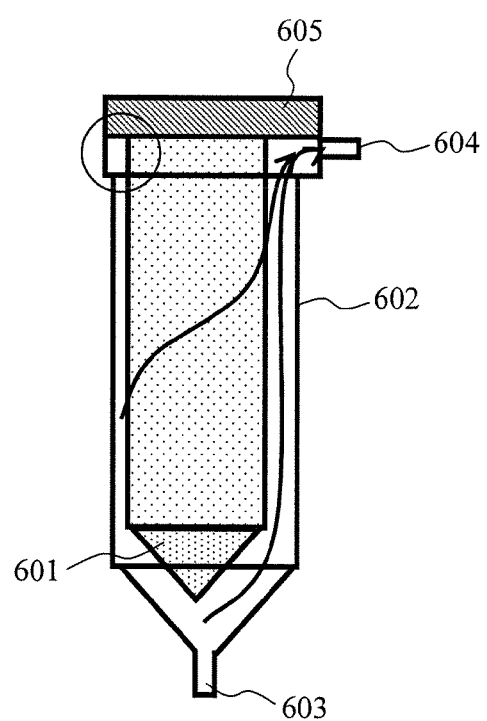

FIG. 6 shows fitting structures of a plunger 601 and a plunger hole 602 forming the plunger pump 202 according to this embodiment. In this embodiment, the plunger 601 and the plunger hole 602 are arranged in such a manner that axes thereof extend in the vertical direction. The plunger 601 and the plunger hole 602 according to this embodiment are also common to those in Embodiment 1 in that the cross-sectional shapes thereof are a circle.

In the case of the plunger 601 according to this embodiment, however, a tip end (the lower side of the drawing) of the plunger 601 is machined into a conical shape. Furthermore, a bottom surface (the lower side of the drawing) of the plunger hole 602 is machined into a funnel shape so that a clearance of a predetermined width can be formed, at the maximum thrusting of the plunger 601, between the bottom surface and the tip end portion of the plunger 601 machined into the conical shape. However, the conical shape is not essential, and a planar structure which is the same as those in Embodiments 1 and 2 may be employed for both the tip end of the plunger 601 and the bottom surface portion of the plunger hole 602. Hereinafter as shown in FIG. 6, the tip end of the plunger 601 and the bottom surface of the plunger hole 602 are both formed into the conical shape.

In this embodiment, an inlet 603 to introduce the electrophoresis medium is formed in the lowermost portion of this plunger hole 602. Furthermore, an outlet 604 to lead out the electrophoresis medium is formed in the uppermost portion (an outer edge portion on the opening side) of the plunger hole 602. Also in this embodiment, however, as long as the inlet 603 is formed at a lower position than the outlet 604 is, the inlet 603 may be formed at any position of the plunger hole 602. Note that an opening of the plunger hole 602 is closed by a plunger seal 605 at an upper position than the outlet 604.

In the same manner as Embodiment 1, this embodiment also employs a structure in which an axis of the plunger hole 602 and an axis of the plunger 601 are intentionally shifted from each other. Specifically, a fitting structure shown in Part (a) of FIG. 6 is employed. In other words, the structure is employed in which a fitting position is designed in the following manner. Specifically, a clearance portion, of a clearance formed between a side surface of the plunger hole 602 and a side surface of the plunger 601, formed on the side opposite from the outlet 604 is made larger than a clearance portion formed on the outlet 604 side.

For example, when the plunger 601 has a diameter of approximately 3 mm to 5 mm and an allowance of 0.05 mm, it is preferable to design the clearance as follows.

A clearance portion formed on the side opposite from the outlet 604 between the plunger hole 602 and the plunger 601: approximately 0.2 mm A clearance portion formed on the outlet 604 side between the plunger hole 602 and the plunger 601: approximately 0.1 mm A clearance portion formed between a bottom surface of the plunger 601 and a bottom surface of the plunger hole 602 at the maximum thrusting of the plunger 601: approximately 0.2 mm to 0.4 mm.

When these conditions are satisfied, the clearance portion between the plunger 601 and the plunger hole 602 formed on the side opposite from the outlet 604 can be prevented from being smaller than the clearance portion between the plunger 601 and the plunger hole 602 formed on the outlet 604 side, even if a dimensional variation or an assembly variation is present. Incidentally, under these conditions, when the plunger 601 is fitted in the plunger hole 602 in such a manner as to be shifted to the right side in the drawing and when a shifting amount is the maximum, the clearance portion on the left side in the drawing is 0.25 mm and the clearance portion on the right side in the drawing is 0.05 mm. On the other hand, when the plunger 601 is fitted in such a manner as to be shifted to the left side in the drawing and when the shifting amount is the maximum, the clearance portion on the left side in the drawing is 0.15 mm and the clearance portion on the right side in the drawing is 0.15 mm.

Thus, use of the plunger pump 202 according to the embodiment makes a flow passage resistance formed on the side opposite from the outlet 604 smaller than a flow passage resistance formed on the outlet 604 side. This means that a structure of a plunger pump having no individual difference of the degree of bubble exiting can be achieved.

Subsequently, how bubbles near the plunger exit will be described by using Part (a) of FIG. 6.

(a) How bubbles on the bottom surface of the plunger 601 flow

When the plunger 601 is thrust, most of the electrophoresis medium on a side surface of the plunger 601 flows upward along the side surface opposite from the outlet 604 and moves to the outlet 604 formed in the uppermost portion of the plunger hole 602. At this time, both an upward viscous force and an upward buoyancy due to the electrophoresis medium flow act on bubbles located on the bottom surface of the plunger 601. Thus, most of bubbles flow along the side opposite from the outlet 604 with the flow of the electrophoresis medium.

(b) How bubbles on the outlet 604 side of the plunger flow

When the plunger 601 is thrust, the electrophoresis medium on the side surface of the plunger 601 flows upward along the clearance formed between the plunger 601 and the plunger hole 602 and flows out from the outlet 604 located in the uppermost portion. At this time, both an upward viscous force and an upward buoyancy due to the electrophoresis medium flow act on bubbles located on the side surface of the plunger 601. Thus, the bubbles move with flow of the electrophoresis medium and go out through the outlet 604.

(c) How Bubbles on the Side Surface of the Plunger Opposite from the Outlet 604 Flow When the plunger 601 is thrust, the electrophoresis medium on the side surface of the plunger 601 flows upward along the clearance formed between the plunger 601 and the plunger hole 602, changes the flow direction to a horizontal direction near the uppermost portion of the plunger hole 602, and lastly flows out to the outlet 604. In this case, both the upward viscous force due to the electrophoresis medium flow and the upward buoyancy act on the bubbles in portions of the plunger hole 602 other than the uppermost portion of the plunger hole 602. In addition, both a lateral viscous force due to the electrophoresis medium flow and the upward buoyancy act on the bubbles near the uppermost portion of the plunger hole 602. However, the direction of the viscous force and the direction of the buoyancy do not have a converse directional relationship. Thus, near the uppermost portion of the plunger hole 602, the bubbles are moved to the outlet 604 due to the viscous force.

As described above, in the case of the plunger pump 202 according to the embodiment, the bubbles are moved due to a synthesis force of the buoyancy and the viscous force acting on the bubbles, or due to the viscous force. This causes the bubbles near the plunger not to stay in the plunger 601 but to easily go out from the outlet 604. Consequently, the bubbles can be removed with a small amount of polymer, and thus a consumption amount of the expensive polymer can be reduced.

How the bubbles flow when the plunger pump 202 according to the embodiment is not used will be described for a reference purpose. If the aforementioned fitting structure is not employed, there is a possibility that the clearance portion, between the plunger hole 602 and the plunger 601, formed on the outlet 604 side is wider than the clearance portion, between the plunger hole 602 and the plunger 601, formed on the side opposite from the outlet 604, as shown in Part (b) of FIG. 6.

Also in this case, it goes without saying that the electrophoresis medium tends to flow to the outlet 604 through a path having the smallest flow passage resistance when the plunger 601 is thrust. In other words, most of the electrophoresis medium flows out from the outlet 604 through the clearance portion, between the plunger hole 602 and the plunger 601, formed on the outlet 604 side. This means that the electrophoresis medium flow through the clearance portion, between the plunger hole 602 and the plunger 601, formed on the side opposite from the outlet 604 has a small flow amount. This means that the lateral flow of the electrophoresis medium near the uppermost portion of the plunger hole 602 has a small flow amount. Thus, the bubbles moving due to the buoyancy through the clearance portion, between the plunger hole 602 and the plunger 601, formed on the side opposite from the outlet 604 easily stay in an encircled region in the drawing.

(5) Embodiment 4

Subsequently, a description is given of a fourth embodiment of the capillary electrophoresis device. A basic structure of the capillary electrophoresis device according to this embodiment is the same as that of Embodiment 1. Hereinafter, a description is given of a structure of the plunger pump 202 according to the embodiment.

Figure 7:
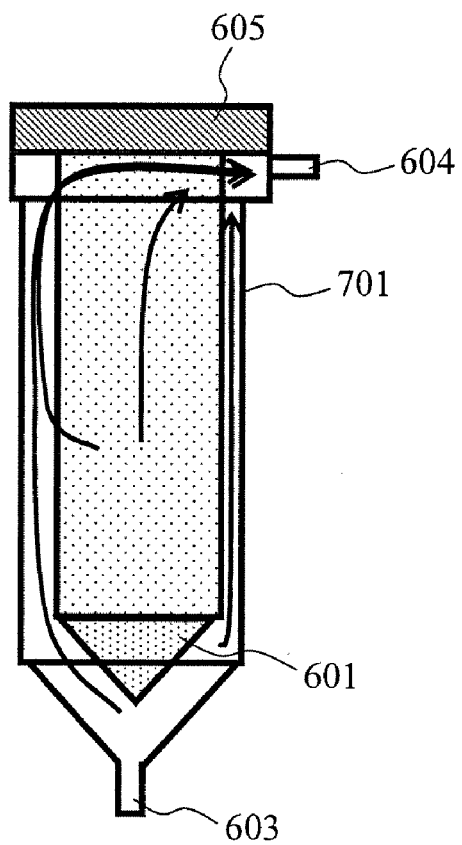
FIGS. 7a and 7b is a diagram for explaining fitting structures of the plunger and the plunger hole according to Embodiment 4.
Figure 7:
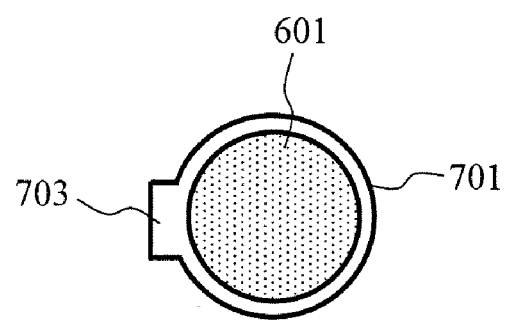

FIG. 7 shows fitting structures of the plunger 601 and a plunger hole 701 forming the plunger pump 202 according to this embodiment. Also in this embodiment, the plunger 601 and the plunger hole 701 are installed extending in the vertical direction, as shown in Part (a) of FIG. 7. In addition, the inlet 603 to introduce the electrophoresis medium is formed in the lowermost portion of the plunger hole 701, and the outlet 604 to lead out the electrophoresis medium is formed in the uppermost portion of the plunger hole 701.

The difference from Embodiment 3 lies in a cross-sectional structure of the plunger hole 701. Part (b) of FIG. 7 shows a cross-sectional shape corresponding to a part taken along the dotted line in Part (a) of FIG. 7. In this embodiment, as shown in Part (b) of FIG. 7, a groove 703 extending in an extending direction of the plunger hole 701 is formed on the side surface, of the plunger hole 701, on the side opposite from the outlet 604. Thus, an inner diameter of the portion in which the groove 703 is formed is formed to be larger than an inner diameter of the other portion.

For example, when the plunger 601 has a diameter of approximately 3 mm to 5 mm and an allowance of 0.05 mm, it is preferable to design the clearance as follows.

A clearance portion formed on the side surface of the groove 703 and the plunger 601: approximately 0.2 mm A clearance portion between the plunger hole 701 and the plunger 601 formed on the outlet 604 side: approximately 0.1 mm A clearance portion formed between a bottom surface of the plunger 601 and a bottom surface of the plunger hole 701 at the maximum thrusting of the plunger 601: approximately 0.2 mm to 0.4 mm.

When these conditions are satisfied, the clearance portion formed between the groove 703 and the plunger 601 can be prevented from being smaller than the clearance portion formed between the plunger hole 701 and the plunger 601 on the outlet 604 side, even if a dimensional variation or an assembly variation is present. The dimensions are determined in consideration of allowances, as a matter of course.

Alternatively, in the case of using the groove 703 as in this embodiment, the fitting position of the plunger 601 and the plunger hole 701 can be designed so that an axis of the plunger hole 701 and the axis of the plunger 601 can coincide with each other, instead of the case where the axis of the plunger hole 701 and the axis of the plunger 601 are shifted from each other as in Embodiment 3. Part (b) of FIG. 7 corresponds to the case where the plunger hole 701 and the plunger 601 are fitted coaxially.

Thus, use of the plunger pump 202 according to this embodiment makes a flow passage resistance formed on the groove 703 side smaller than a flow passage resistance formed on the outlet 604 side. This means that a structure of a plunger pump having no individual difference of the degree of bubble exiting can be achieved.

Consequently, the bubbles in this embodiment flow in the same manner as that in Embodiment 3. Specifically, in the case of the plunger pump 202 according to the embodiment, the bubbles are moved by a combination force of the buoyancy and the viscous force acting on the bubbles or by a viscous force acting thereon. This causes the bubbles near the plunger not to stay in the plunger 601 but to easily go out from the outlet 604. Consequently, the bubbles can be removed with a small amount of polymer, and thus a consumption amount of the expensive polymer can be reduced.

(6) Embodiment 5

Subsequently, a description is given of a fifth embodiment of the capillary electrophoresis device. A basic structure of the capillary electrophoresis device according to this embodiment is the same as that of Embodiment 1. Hereinafter, a description is given of a structure of the plunger pump 202 according to the embodiment.

Figure 8:
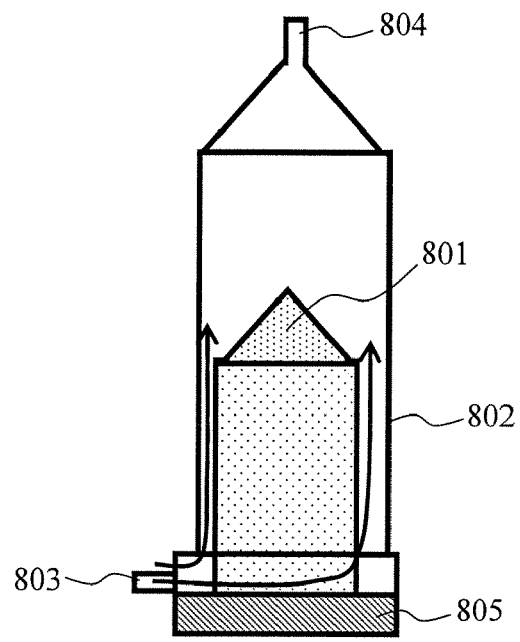
FIGS. 8a and 8b is a diagram for explaining fitting structures of the plunger and the plunger hole according to Embodiment 5.
Figure 8:
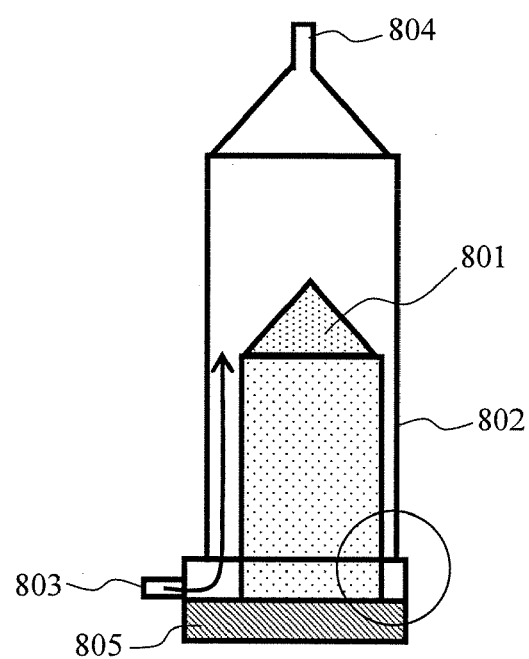

FIG. 8 shows fitting structures of the plunger 801 and a plunger hole 802 forming the plunger pump 202 according to this embodiment. Also in this embodiment, in the same manner as Embodiments 3 and 4, the plunger 801 and the plunger hole 802 are arranged in such a manner that axes thereof extend in the vertical direction. In addition, the plunger 801 and the plunger hole 802 according to this embodiment are also common to those in Embodiment 3 in that the cross-sectional shapes thereof are a circle.

However, in the plunger pump 202 according to this embodiment, the plunger 801 moves in a direction reverse to that in Embodiment 3 when the electrophoresis medium is injected into a syringe. To put it differently, in Embodiment 3 (FIG. 6), the description has been given of the example in which the plunger 601 is thrust from the upper portion in the vertical direction to the lower portion. This embodiment, however, assumes that a case where the plunger 801 is pulled back from the lower portion in the vertical direction to the upper portion. Thus, an opening of the plunger hole 802 is arranged on the lower side in the vertical direction, and an inlet 803 for the electrophoresis medium is arranged on the opening side. In addition, the opening of the plunger hole 802 is closed by a plunger seal 805 at the position lower than the inlet 803.

A tip end (upper side of the drawing) of the plunger 801 is machined into a conical shape, like Embodiment 3. Furthermore, a top surface (the upper side of the drawing) of the plunger hole 802 is machined into a funnel shape so that a clearance of a predetermined width can be formed, at the maximum pull-back of the plunger 801, between the top surface and the tip end portion of the plunger 801 machined into the conical shape. Thus, in this embodiment, an outlet 804 for the electrophoresis medium is formed in the uppermost portion of the top surface of the plunger hole 802 machined into the conical shape.

However, the conical shape is not essential, and a planar structure which is the same as those in Embodiments 1 and 2 may be employed for both the tip end of the plunger 801 and the top surface portion of the plunger hole 802. As described above, in the case where the top surface has the planer shape, the outlet 804 may be formed in any portion as long as the outlet 804 is located in the uppermost portion of the plunger hole 802.

Hereinafter, the tip end of the plunger 801 and the top surface of the plunger hole 802 are both formed into the conical shape, as shown in FIG. 8.

In the same manner as Embodiment 3, this embodiment also employs a structure in which an axis of the plunger hole 802 and an axis of the plunger 801 are intentionally shifted from each other. Specifically, a fitting structure shown in Part (a) of FIG. 8 is employed. In other words, the structure is employed in which a fitting position is designed in the following manner. Specifically, a clearance portion, of a clearance formed between a side surface of the plunger hole 802 and a side surface of the plunger 801, formed on the side opposite from the inlet 803 is made larger than a clearance portion formed on the inlet 803 side.

For example, when the plunger 801 has a diameter of approximately 3 mm to 5 mm and an allowance of 0.05 mm, it is preferable to design the clearance as follows.

A clearance portion formed on the side opposite from the inlet 803 between the plunger hole 802 and the plunger 801: approximately 0.2 mm A clearance portion formed on the inlet 803 side between the plunger hole 802 and the plunger 801: approximately 0.1 mm A clearance portion formed between a bottom surface of the plunger 801 and a top surface of the plunger hole 802 at the maximum pull-back of the plunger 801: approximately 0.2 mm to 0.4 mm.

When these conditions are satisfied, the clearance portion between the plunger 801 and the plunger hole 802 formed on the side opposite from the inlet 803 can be prevented from being smaller than the clearance portion between the plunger 801 and the plunger hole 802 formed on the inlet 803 side, even if a dimensional variation or an assembly variation is present. Incidentally, under these conditions, when the plunger 801 is fitted in the plunger hole 802 in such a manner as to be shifted to the left side in the drawing and when a shifting amount is the maximum, the clearance portion on the right side in the drawing is 0.25 mm and the clearance portion on the left side in the drawing is 0.05 mm. On the other hand, when the plunger 801 is fitted in such a manner as to be shifted to the right side in the drawing and when the shifting amount is the maximum, the clearance portion on the left side in the drawing is 0.15 mm and the clearance portion on the right side in the drawing is 0.15 mm.

Thus, use of the plunger pump 202 according to this embodiment makes a flow passage resistance formed on the side opposite from the inlet 803 smaller than a flow passage resistance formed on the inlet 803 side. This means that a structure of a plunger pump having no individual difference of the degree of bubble exiting can be achieved.

Subsequently, how bubbles near the plunger exit will be described by using Part (a) of FIG. 8.

(a) How bubbles near a lower end of a side surface of the plunger flow

A buoyancy acts on bubbles. In addition, in this embodiment, a flow passage resistance of a clearance portion formed on the side opposite from the inlet 803 is designed to be smaller than a flow passage resistance of a clearance portion formed on the inlet 803 side. For this reason, when the plunger 801 is pulled back, a satisfactorily large amount of electrophoresis medium flow occurs not only in a vicinity of the inlet 803 but also in a vicinity of the back of the plunger 801 viewed from the inlet 803 side. Thus, the viscous force of the electrophoresis medium in addition to the buoyancy acts on the bubbles. Thereby, the bubbles move upward away from the plunger 801.

(b) How bubbles on a side surface of the inlet side of the plunger flow

A buoyancy acts on bubbles. In this embodiment, the clearance portion, between the plunger 801 and the plunger hole 802, formed on the inlet 803 side is smaller than the clearance portion formed on the side opposite from the inlet 803. For this reason, the relative magnitude of the electrophoresis medium flow through the clearance portion on the inlet 803 side is smaller than that of the flow on the side opposite from the inlet 803. However, the flow passage naturally has an upward flow due to the electrophoresis medium. Thus, both the buoyancy and the viscous force of the electrophoresis medium act on the bubbles. Thereby, the bubbles move away from the side surface of the plunger 801 toward the outlet 804.

(c) How Bubbles on the Plunger Seal Near the Inlet 803 Flow

When the plunger 801 is pulled back, the electrophoresis medium flows from the inlet 803 to the plunger hole 802. At this time, some of the electrophoresis medium flows along a surface of the plunger seal 805, and the other flows upward along the clearance formed between the plunger 801 and the plunger hole 802. Thus, both the viscous force acting horizontally or upward due to the electrophoresis medium flow, and the upward buoyancy act on the bubbles. Accordingly, the bubbles move to the outlet 804 with the flow of the electrophoresis medium.

(d) How Bubbles on the Plunger Seal 805 on the Side Opposite from the Inlet 803 Flow When the plunger 801 is pulled back, the electrophoresis medium flows from the inlet 803 to the plunger hole 802. Meanwhile, the flow passage resistance of the clearance portion formed on the side opposite from the inlet 803 is smaller than the flow passage resistance of the clearance portion formed on the inlet 803 side. For this reason, most of the electrophoresis medium flowing from the inlet 803 is supplied along the surface of the plunger seal 805 to reach the side opposite from the inlet 803. Thus, a satisfactorily large amount of electrophoresis medium flow exists near the plunger seal 805 located on the side opposite from the inlet 803. Specifically, the electrophoresis medium flowing from the inlet 803 soon changes the flow direction to flow upward, and moves upward along the side surface of the plunger hole 802. For this reason, both the viscous force acting horizontally or upward due to the electrophoresis medium and the upward buoyancy act on the bubbles on the plunger seal 805 on the side opposite from the inlet 803. Thus, the bubbles move away from the plunger seal 805 to the outlet 804 along a side wall of the plunger hole 802 together with the electrophoresis medium.

As described above, the case of the plunger pump 202 according to the embodiment enables not only the buoyancy but also the viscous force generated with the movement of the electrophoresis medium to act on the bubbles, in whichever portion near the plunger 801 and the plunger hole 802 the bubbles are located (in particular, even if the bubbles are present near the back surface, of the plunger 801, viewed from the inlet 803).

This causes the bubbles near the plunger seal 805 not to stay in the vicinity of the plunger seal 805 but to easily go out from the outlet 804. Consequently, the bubbles can be removed with a small amount of polymer, and thus a consumption amount of the expensive polymer can be reduced.

How the bubbles flow when the plunger pump 202 according to the embodiment is not used will be described for a reference purpose. If the aforementioned fitting structure is not employed, there is a possibility that the clearance portion, between the plunger hole 802 and the plunger 801, formed on the inlet 803 side is wider than the clearance portion, between the plunger hole 802 and the plunger 801, formed on the side opposite from the inlet 803, as shown in Part (b) of FIG. 8.

Also in this case, it goes without saying that the electrophoresis medium tends to flow to the outlet 804 through a path having the smallest flow passage resistance when the plunger 801 is pulled back. In other words, most of the electrophoresis medium flows out from the outlet 804 through the clearance portion, between the plunger hole 802 and the plunger 801, formed on the inlet 803 side. This means that the electrophoresis medium flow through the clearance portion, between the plunger hole 802 and the plunger 801, formed on the side opposite from the inlet 803 has a small flow amount.

To put it differently, this means that the electrophoresis medium flow along the surface of the plunger seal 805 also has a small flow amount. Accordingly, most of the force acting on the bubbles on the vicinity of the plunger seal 805 is the buoyancy only. However, only the buoyancy is not enough as a force to move the bubbles. For this reason, the bubbles easily stay on the side opposite from the inlet 803 in an encircled regional portion in the drawing.

(7) Embodiment 6

Subsequently, a description is given of a sixth embodiment of the capillary electrophoresis device. A basic structure of the capillary electrophoresis device according to this embodiment is the same as that of Embodiment 5. Hereinafter, a description is given of a structure of the plunger pump 202 according to the embodiment.

Figure 9:
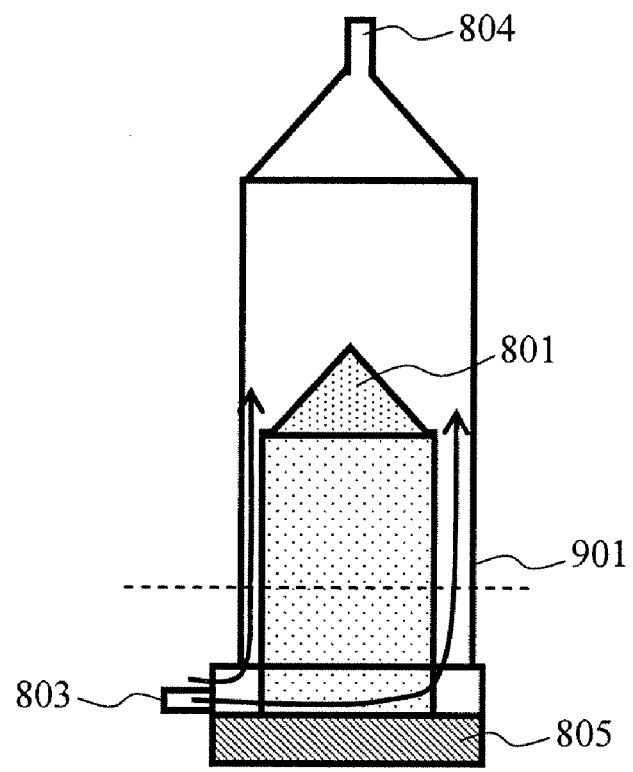
FIGS. 9a and 9b is a diagram for explaining fitting structures of the plunger and the plunger hole according to Embodiment 6.
Figure 9:
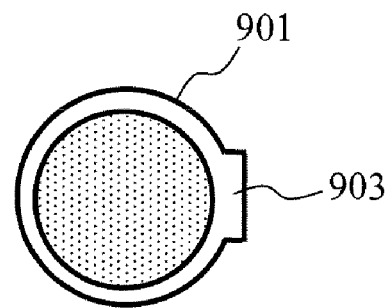

FIG. 9 shows fitting structures of the plunger 801 and a plunger hole 901 forming the plunger pump 202 according to this embodiment. Also in this embodiment, as shown in Part (a) of FIG. 9, the plunger 801 and the plunger hole 901 are arranged extending in the vertical direction. In addition, the inlet 803 to introduce the electrophoresis medium is formed in the lowermost portion of the plunger hole 901, and the outlet 804 to lead out the electrophoresis medium is formed in the uppermost portion of the plunger hole 901.

The difference from Embodiment 5 lies in a cross-sectional structure of the plunger hole 901. Part (b) of FIG. 9 shows a cross-sectional shape corresponding to a part taken along the dotted line in Part (a) of FIG. 9. In this embodiment, as shown in Part (b) of FIG. 9, a groove 903 extending in an extending direction of the plunger hole 901 is formed on the side surface, of the plunger hole 901, opposite from the inlet 803. Thus, an inner diameter of the portion in which the groove 903 is formed is formed to be larger than an inner diameter of the other portion.

For example, when the plunger 801 has a diameter of approximately 3 mm to 5 mm and an allowance of 0.05 mm, it is preferable to design the clearance as follows.

A clearance portion formed between the side surface of the groove 903 and the side surface of the plunger 801: approximately 0.2 mm A clearance portion formed on the inlet 803 side between the plunger hole 901 and the plunger 801: approximately 0.1 mm A clearance portion formed between a top surface of the plunger 801 and a top surface of the plunger hole 901 at the maximum pull-back of the plunger 801: approximately 0.2 mm to 0.4 mm.

When these conditions are satisfied, the clearance portion formed between the plunger 801 and the groove 903 can be prevented from being smaller than the clearance portion formed on the inlet 803 side between the plunger 801 and the plunger hole 901, even if a dimensional variation or an assembly variation is present. The dimensions are determined in consideration of allowances, as a matter of course.

Alternatively, in the case of using the groove 903 as in this embodiment, the fitting position of the plunger 801 and the plunger hole 901 can be designed so that an axis of the plunger hole 901 and the axis of the plunger 801 can coincide with each other, instead of the case where the axis of the plunger hole 901 and the axis of the plunger 801 are shifted from each other as in Embodiment 5. Part (b) of FIG. 9 corresponds to the case where the plunger hole 901 and the plunger 801 are fitted coaxially.

Accordingly, use of the plunger pump 202 according to this embodiment enables the flow passage resistance formed on the groove 903 side to be smaller than the flow passage resistance on the inlet 803 side. This means that a structure of a plunger pump having no individual difference of the degree of bubble exiting can be achieved.

Consequently, the bubbles in this embodiment flow in the same manner as that in Embodiment 5. In sum, the case of the plunger pump 202 according to the embodiment enables both the buoyancy and the viscous force to act on the bubbles, in whichever location of the plunger seal 805 the bubbles are present. This causes the bubbles, viewed from the inlet 803, located on the back side of the plunger seal 805 not to stay on the surface of the plunger seal 805 but to easily go out from the outlet 804. Consequently, the bubbles can be removed with a small amount of polymer, and thus a consumption amount of the expensive polymer can be reduced.

(8) Embodiment 7

Subsequently, a description is given of a seventh embodiment of the capillary electrophoresis device. A basic structure of the capillary electrophoresis device according to this embodiment is the same as that of Embodiment 1. Hereinafter, a description is given of a structure of the plunger pump 202 according to the embodiment.

Figure 10:
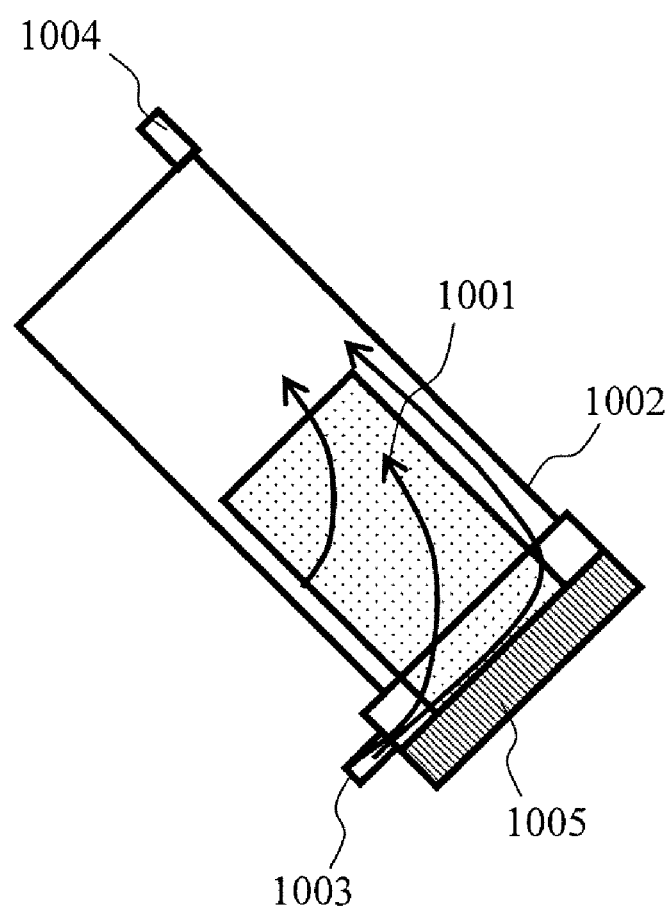
FIG. 10 is a diagram for explaining fitting structures of the plunger and the plunger hole according to Embodiment 7.

FIG. 10 shows fitting structures of the plunger 1001 and a plunger hole 1002 forming the plunger pump 202 according to this embodiment. Also in this embodiment, the plunger 1001 and the plunger hole 1002 are arranged in such a manner as to extend obliquely to the vertical direction, as in Embodiment 1. In addition, the plunger 1001 and the plunger hole 1002 according to this embodiment are common to those in Embodiment 1 in that the cross-sectional shapes thereof are a circle.

However, in the plunger pump 202 according to this embodiment, the plunger 1001 moves in a direction reverse to that in Embodiment 1 when the electrophoresis medium is injected into a syringe. That is, in Embodiment 1 (FIG. 4), the description has been given of the example in which the plunger 304 is thrust from the obliquely upper portion in the vertical direction to the obliquely lower portion. However, this embodiment assumes a case where the plunger 1001 is pulled back from the obliquely lower portion in the vertical direction to the obliquely upper portion. Thus, an opening of the plunger hole 1002 is arranged on the lower side in the vertical direction, and an inlet 1003 for the electrophoresis medium is arranged on the opening side. In addition, the opening of the plunger hole 1002 is closed by a plunger seal 1005 at the position lower than the inlet 1003. Meanwhile, an outlet 1004 to lead out the electrophoresis medium is formed in the uppermost portion of the plunger hole 1002.

Note that the structure of the other portions of the plunger pump 202 is the same as that in Embodiment 1. In other words, a fitting position is designed in the following manner. A clearance portion, of a clearance formed between a side surface of the plunger hole 1002 and a side surface of the plunger 1001, formed on an upper side in the vertical direction is made larger than a clearance portion formed on the lower side in the vertical direction. Thus, also in the case of the plunger pump 202 according to this embodiment, the flow passage resistance on the upper surface side of the plunger 1001 can be made smaller than the flow passage resistance on the lower surface side. This means that a structure of a plunger pump having no individual difference of the degree of bubble exiting can be achieved.

Subsequently, how bubbles near the plunger exit will be described by using FIG. 10.

(a) How Bubbles on the Side Surface of the Plunger Flow

When the plunger 1001 is pulled back, the electrophoresis medium on the side surfaces of the plunger 1001 and the plunger hole 1002 are all at once thrust toward the outlet 1004 located in the uppermost portion of the plunger hole 1002. At this time, the electrophoresis medium moves upward along the surface of the plunger 1001. In addition, as described in Embodiment 1, a large amount of flow due to the movement of the electrophoresis medium occurs also in the clearance portion on the back side, of the plunger 1001, viewed from the inlet 1003. Thus, it is possible to cause the upward viscous force due to the electrophoresis medium to act also on bubbles on the back surface, of the plunger 1001, viewed from the inlet 1003. As the result, both the viscous force due to the electrophoresis medium and the buoyancy act on the bubbles. Accordingly, the bubbles move with the flow of the electrophoresis medium to go out through the outlet 1004.

(b) How Bubbles on the Plunger Seal Flow

When the plunger 1001 is pulled back, the electrophoresis medium flows from the inlet 1003.

As described above, a clearance portion, of the clearance formed by the plunger 1001 and the plunger hole 1002, formed on the upper side in the vertical direction is formed to be larger than the other, in the case of the plunger pump 202 according to this embodiment. That is, the clearance portion is formed to have a small flow passage resistance. Thus, some of the electrophoresis medium moves along a surface of the plunger seal 1005. This means that in whichever location of the plunger seal 1005 the bubbles are present, both the upward viscous force due to the electrophoresis medium flow and the upward buoyancy act on the bubbles. Accordingly, the bubbles move with the flow of the electrophoresis medium to go out through the outlet 1004.

As described above, in the case of the plunger pump 202 according to the embodiment, the bubbles also on the plunger seal 1005 easily go out from the outlet 1004 without staying thereon. Consequently, the bubbles can be removed with a small amount of polymer, and thus the consumption amount of the expensive polymer can be reduced.

(9) Embodiment 8

Subsequently, a description is given of an eighth embodiment of the capillary electrophoresis device. A basic structure of the capillary electrophoresis device according to this embodiment is the same as that of Embodiment 1. Hereinafter, a description is given of a structure of the plunger pump 202 according to the embodiment.

Figure 11:
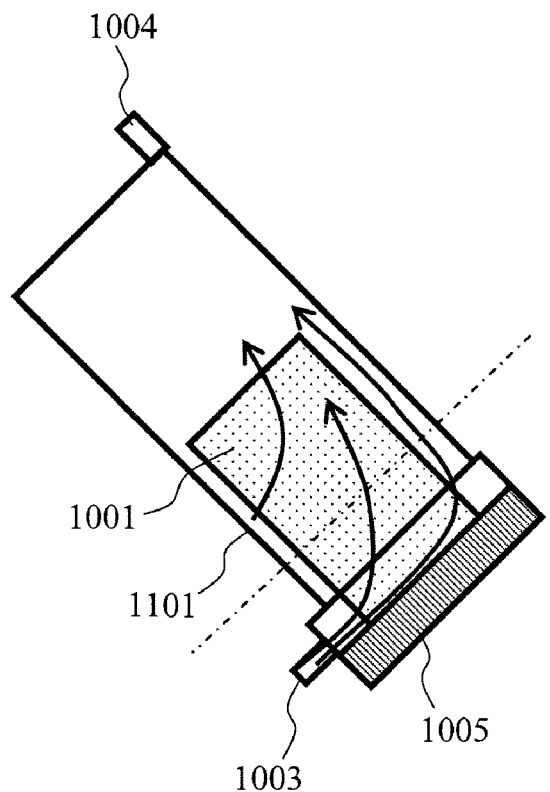
FIGS. 11a and 11b is a diagram for explaining fitting structures of the plunger and the plunger hole according to Embodiment 8.
Figure 11:
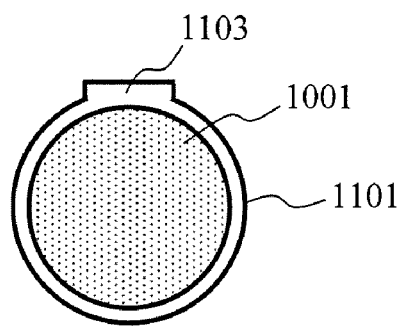

FIG. 11 shows fitting structures of a plunger 1001 and a plunger hole 1101 forming the plunger pump 202 according to this embodiment. A basic structure according to this embodiment is the same as that of Embodiment 7 (FIG. 10). Specifically, the plunger 1001 and the plunger hole 1101 are installed obliquely to the vertical direction. In addition, an inlet 1003 to introduce the electrophoresis medium is formed in the lowermost portion of the plunger hole 1101, and an outlet 1004 to lead out the electrophoresis medium is formed in the uppermost portion of the plunger hole 1101.

The difference from Embodiment 7 lies in a cross-sectional structure of the plunger hole 1101. Part (b) of FIG. 11 shows a cross-sectional shape corresponding to a part taken along the dotted line in Part (a) of FIG. 11. In this embodiment, as shown in Part (b) of FIG. 11, a groove 1103 extending in an extending direction of the plunger hole 1101 is formed on the upper surface side of the plunger hole 1101 in the vertical direction. Thus, an inner diameter of the portion in which the groove 1103 is formed is formed to be larger than an inner diameter of the other portion.

For example, when the plunger 1001 has a diameter of approximately 3 mm to 5 mm, an inclination in a fitting direction of 25° with respect to a horizontal surface (65° with respect to the vertical direction), and an allowance of 0.05 mm, it is preferable to design the clearance as follows.

A clearance portion formed between the bottom surface of the groove 1103 (the upper surface side of the plunger hole 1101) and the plunger 1001: approximately 0.2 mm A clearance portion formed between the lower surface side of the plunger 1001 and the plunger hole 1101: approximately 0.1 mm A clearance portion formed between a top surface of the plunger 1001 and a top surface of the plunger hole 1101 at the maximum pull-back of the plunger 1001: approximately 0.2 mm to 0.4 mm.

When these conditions are satisfied, the clearance portion formed between the plunger 1001 and the groove 1103 on the upper side in the vertical direction can be prevented from being smaller than the clearance portion formed between the plunger 1001 and the groove 1103 on the lower side in the vertical direction, even if a dimensional variation or an assembly variation is present. The dimensions are determined in consideration of allowances, as a matter of course.

Alternatively, in the case of using the groove 1103 as in this embodiment, the fitting position of the plunger 1001 and the plunger hole 1101 can be designed so that an axis of the plunger hole 1101 and the axis of the plunger 1001 can coincide with each other, instead of the case where the axis of the plunger hole 1101 and the axis of the plunger 1001 are shifted from each other as in Embodiment 7. Part (b) of FIG. 11 corresponds to the case where the plunger hole 1101 and the plunger 1001 are fitted coaxially.

Accordingly, use of the plunger pump 202 according to this embodiment enables the flow passage resistance formed on the plunger 1001 on the upper side in the vertical direction to be smaller than the flow passage resistance formed on the plunger 1001 on the lower side in the vertical direction. This means that a structure of a plunger pump having no individual difference of the degree of bubble exiting can be achieved.

Subsequently, how bubbles near the plunger exit will be described by using FIG. 11.

(a) How bubbles on a side surface of the plunger flow

When the plunger 1001 is pulled back, the electrophoresis medium on a side surface of the plunger 1001 is all at once thrust toward the outlet 1004 located in the uppermost portion of the plunger hole 1101. At this time, the electrophoresis medium moves upward along the surface of the plunger 1001. In addition, a large amount of flow due to the movement of the electrophoresis medium along the groove 1103 occurs also in the clearance portion on the back side, of the plunger 1001, viewed from the inlet 1003. Thus, it is possible to cause the upward viscous force due to the electrophoresis medium to act also on bubbles on the back surface, of the plunger 1001, viewed from the inlet 1003. As the result, both the viscous force due to the electrophoresis medium and the buoyancy act on the bubbles. Accordingly, the bubbles move with the flow of the electrophoresis medium to go out through the outlet 1004.

(b) How Bubbles on the Plunger Seal Flow

When the plunger 1001 is pulled back, the electrophoresis medium flows from the inlet 1003. As described above, in the case of the plunger pump 202 according to the embodiment, a clearance portion formed in the groove 1103 portion is formed to be larger than that in the other portion. That is, the clearance portion is formed to have a small flow passage resistance along the groove 1103. Thus, some of the electrophoresis medium reaches a portion as well, of the plunger seal 1005, farther than the plunger 1001 viewed from the inlet 1003. This means that in whichever location of the plunger seal 1005 the bubbles are present, both the upward viscous force due to the electrophoresis medium flow and the upward buoyancy act on the bubbles. Thus, the bubbles move with the flow of the electrophoresis medium and go out through the outlet 1004.

As described above, in the case of the plunger pump 202 according to the embodiment, it is possible to cause the bubbles near the plunger seal 1005 not to stay in the vicinity of the plunger seal 1005 but to easily go out from the outlet 1004. Consequently, the bubbles can be removed with a small amount of polymer, and thus a consumption amount of the expensive polymer can be reduced.

(10) Embodiment 9

Subsequently, a description is given of a ninth embodiment of the capillary electrophoresis device. A basic structure of the capillary electrophoresis device according to this embodiment is the same as that of Embodiment 1. This embodiment focuses on the rate of driving a plunger, unlike the aforementioned embodiments.

Specifically, when the electrophoresis medium is injected into the capillary (when the electrophoresis medium is discharged from the plunger pump), the plunger drive rate is increased to increase the flow rate of the electrophoresis medium. This can enhance the viscosity viscous force acting on bubbles.

In contrast, when the capillary is refilled with the electrophoresis medium (when the electrophoresis medium is filled into the plunger pump), the plunger is quickly driven in a reverse direction. This can lowers the air pressure in the plunger hole. Lowering the air pressure in this manner makes the bubbles larger and thus increases the buoyancy acting on the bubbles.

Note that each of the drive rates can be achieved by setting the drive rate at the maximum rate within a range where a motor of a plunger pump 203 does not step out. Consequently, the bubbles can be removed with a small amount of polymer, and thus a consumption amount of the expensive polymer can be reduced.

Note that this technique can exert the effects in the aforementioned embodiments to the maximum extent by combining the embodiments. This specification also discloses the combination of the embodiments.

EXPLANATION OF THE REFERENCE NUMERALS 101, 403, 503, 602, 701, 802, 901, 1002, 1101 . . . plunger hole, 102, 304, 601, 801, 1001 . . . plunger, 103, 404, 605, 805, 1005 . . . plunger seal, 104, 402, 604, 804, 1004 . . . outlet, 401, 603, 803, 1003 . . . inlet, 505, 703, 903, 1103 . . . groove.

The invention claimed is:

1. An electrophoresis device comprising:
   at least one capillary to be filled with an electrophoresis medium;
   a voltage source that applies a voltage to ends of the capillary;
   an optical detection mechanism that optically detects a sample separated by electrophoresis in the capillary; and
   a pump which includes a tubular container arranged obliquely to a vertical direction, a plunger operated along an inner wall of the container, an outlet through which the electrophoresis medium is filled into the capillary, and an inlet through which the electrophoresis medium is caused to flow into the container and which has a clearance formed between a side wall of the container and a side wall of the plunger in such a manner that a portion of the clearance in a region on an upper side in the vertical direction has a cross-sectional area larger than a cross-sectional area of the other portion of the clearance.

2. The electrophoresis device according to claim 1, characterized by being assembled in such a manner that an axis of the plunger is eccentric to an axis of the container downward in the vertical direction.

3. The electrophoresis device according to claim 1, characterized in that the container has a groove in the sidewall thereof on the upper side in the vertical direction, the groove increasing an inner diameter of the container.

4. An electrophoresis device characterized by comprising:
   at least one capillary to be filled with an electrophoresis medium;
   a voltage source that applies a voltage to ends of the capillary;
   an optical detection mechanism that optically detects a sample separated by electrophoresis in the capillary; and
   a pump which includes a tubular container arranged in a vertical direction, a plunger operated along an inner wall of the container, an outlet through which the electrophoresis medium is filled into the capillary, and an inlet through which the electrophoresis medium is caused to flow into the container, and which has a clearance formed between a side wall of the container and a side wall of the plunger in such a manner that a portion of the clearance in a region increasing a length of a path from the inlet to the outlet has a cross-sectional area larger than a cross-sectional area of the other portion of the clearance.

5. The electrophoresis device according to claim 4, characterized in that the portion of the clearance formed to be larger than the other portion of the clearance is formed on a side surface opposite from a side surface having the outlet formed therein.

6. The electrophoresis device according to claim 5, characterized by being assembled in such a manner that an axis of the plunger is eccentric to an axis of the container toward the outlet.

7. The electrophoresis device according to claim 5, characterized in that the container has a groove in the side wall opposite from the outlet, the groove increasing an inner diameter of the container.

8. The electrophoresis device according to claim 4, characterized in that the portion of the clearance formed to be larger than the other portion of the clearance is formed on a side surface opposite from a side surface having the inlet formed therein.

9. The electrophoresis device according to claim 8, characterized by being assembled in such a manner that an axis of the plunger is eccentric to an axis of the container toward the inlet.

10. The electrophoresis device according to claim 8, characterized in that the container has a groove in the side wall opposite from the inlet, the groove increasing an inner diameter of the container.

11. A pump comprising:
    a tubular container arranged obliquely to a vertical direction;
    a plunger operated along an inner wall of the container;
    an outlet; and
    an inlet, the pump having
    a clearance formed between a side wall of the container and a side wall of the plunger in such a manner that a portion of the clearance in a region on an upper side in the vertical direction has a cross-sectional area larger than a cross-sectional area of the other portion of the clearance.

12. The pump according to claim 11, characterized by being assembled in such a manner that an axis of the plunger is eccentric to an axis of the container downward in the vertical direction.

13. The electrophoresis device according to claim 11, characterized in that the container has a groove in the side wall thereof on the upper side in the vertical direction, the groove increasing an inner diameter of the container.

14. A pump comprising:
    a tubular container arranged in a vertical direction;
    a plunger operated along an inner wall of the container;
    an outlet; and
    an inlet; the pump having
    a clearance formed between a side wall of the container and a side wall of the plunger in such a manner that a portion of the clearance in a region increasing a length of a path from the inlet to the outlet has a cross-sectional area larger than a cross-sectional area of the other portion of the clearance.

15. The pump according to claim 14, characterized in that the portion of the clearance formed to be larger than the other portion of the clearance is formed on a side surface opposite from a side surface having the outlet formed therein.

16. The pump according to claim 15, characterized by being assembled in such a manner that an axis of the plunger is eccentric to an axis of the container toward the outlet.

17. The pump according to claim 15, characterized in that the container has a groove in a side wall opposite from the outlet, the groove increasing an inner diameter of the container.

18. The pump according to claim 14, characterized in that the portion of the clearance formed to be larger than the other portion of the clearance is formed on a side surface opposite from a side surface having the inlet formed therein.

19. The pump according to claim 18, characterized by being assembled in such a manner that an axis of the plunger is eccentric to an axis of the container toward the inlet.

20. The pump according to claim 18, characterized in that the container has a groove in a side wall opposite from the inlet, the groove increasing an inner diameter of the container.

* * * * *